US006063985A

United States Patent [19]
Chua et al.

[11] Patent Number: 6,063,985
[45] Date of Patent: May 16, 2000

[54] CHEMICAL INDUCIBLE PROMOTOR USED TO OBTAIN TRANSGENIC PLANTS WITH A SILENT MARKER

[75] Inventors: Nam-Hai Chua, Scarsdale, N.Y.; Takashi Aoyama, Shiga, Japan

[73] Assignee: The Rockefeller University, New York, N.Y.

[21] Appl. No.: 09/014,592

[22] Filed: Jan. 28, 1998

[51] Int. Cl.[7] ............................. C12N 15/82; C12N 5/04; C12N 15/29; A01H 5/00
[52] U.S. Cl. ......................... 800/278; 800/287; 800/290; 800/295; 800/298; 800/300; 435/468
[58] Field of Search ................................... 800/278, 287, 800/290, 295, 298, 300; 435/468

[56] References Cited

PUBLICATIONS

Napoli et al. the Plant Cell. 1989. vol. 2: 278–289.
Li et al. Dece Biol. 1992. vol. 153: 386–395.
Tamaoki et al. Plant Cell Physiol. 1997. vol. 38P 917–927.
Ebinuma et al. Proc. Natl Acad. Sci. 1997. Mar. issue. vol. 94: 2117–2121.
Schena et al. Proc. Natl. Acad. Sci. 1991. vol. 188: 10421–10425.
Gan et al. Science. 1995. vol. 270: 1986–1988.
Smigocki et al. Plant Molecular Biology. 1993. vol. 23: 325–335.
Kakimoto et al. Science. 1996. vol. 274: 982–985.
Chuck et al. Plant Cell. 1996. vol. 8: 1277–1289.
Aoyama, T. and Chua, N–H. (1997). "A glucocorticoid–mediated transcriptional induction system in transgenic plants", *The Plant Journal* 11:605–612.
Kakimoto, T. (1996). "CKI1, a Histidine Kinase Homolog Implicated in Cytokinin Signal Transduction"*Science* 274:982–985.
Aoyama, T. et al. (1995). "Ectopic Expression of the Arabidopsis Transcriptional Activator Athb–1 Alters Leaf Cell Fate in Tobacco", *The Plant Cell* 7:1773–1785.
Klee, H.J. and Lanahan, M.B. (1995). "E2. Transgenic Plants in Hormone Biology", in *Plant Hormones* (ed. P.J. Davies) (Kluwer Academic Publishers (Netherlands)), pp. 340–353.
Morris, R.O. (1995). "E. Molecular Aspects of Hormone Synthesis and Action. E1. Genes Specifying Auxin and Cytokinin Biosynthesis in Prokaryotes", in *Plant Hormones* (ed. P.J. Davies) (Kluwer Academic Publishers (Netherlands)), pp. 318–339.
Pareddy, D. et al. (1997). "Maize Transformation Via Helium Blasting", *Maydica* 42:143–154.
Lyon, B.R. et al. (1993). "Cotton plants transformed with a bacterial degradation gene are protected from accidental spray drift damage by the herbicide 2,4–dichlorophenoxyacetic acid", *Transgenic Research* 2:162–169.
Lyon, B.R. et al. (1989). "Expression of a bacterial gene in transgenic tobacco plants confers resistance to the herbicide 2,4–dichlorophenoxyacetic acid", *Plant Molecular Biology* 13:533–540.
Faiss, M. et al. "Conditional transgenic expression of the ipt gene indicates a function for cytokinins in paracrine signaling in whole tobacco plants", *The Plant Journal* 12:401–415.
Smigocki, A.C. (1991). "Cytokinin content and tissue distribution in plants transformed by a reconstructed isopentenyl transferase gene", *Plant Molecular Biology* 16:105–115.
Abel, S. and Theologis, A. (1994). "Transient transformation of Arabidopsis leaf protoplasts: a versatile experimental system to study gene expression", *The Plant Journal* 5:421–427.
Thomas, J.C. et al. (1995). "Light–induced expression of ipt from Agrobacterium tumefaciens results in cytokinin accumulation and osmotic stress symptoms in transgenic tobacco ", *Plant Molecular Biology* 27:225–235 and Erratum.
Shinmyo, A. et al. (1996). "Construction of Gene Expression System in Cultured Tobacco Cells", *Ann. N. Y. Acad. Sci.* 782:97–106.
De Veylder, L. et al. (1997). "Herbicide Safener–Inducible Gene Expression in Arabidopsis thaliana", *Plant Cell Physiol.* 38:568–577.
Schena, M. et al. (1991). "A steroid–inducible gene expression system for plant cells", *Proc. Natl. Acad. Sci. USA* 88:10421–10425.
Lieber, J.G. and Evans, R.M. (1996). "Disruption of the vimentin intermediate filament system during adipose conversion of 3T3–L1 cells inhibits lipid droplet accumulation", *J. Cell Science* 109:3047–3058.
Lincoln, C. et al. (1994). "A knotted1–like Homeobox Gene in Arabidopsis is Expressed in the Vegetative Meristem and Dramatically Alters Leaf Morphology When Overexpressed in Transgenic Plants", *The Plant Cell* 6:1859–1876.
Chuck, G. et al. (1996). "KNAT1 Induces Lobed Leaves with Ectopic Meristems Whem Overexpressed in Arabidopsis", *The Plant Cell* 8:1277–1289.
Ludwig, S.R. et al. (1989). "Lc, a member of the maize R gene family responsible for tissue–specific anthocyanin production, encodes a protein similar to transcriptional activators and contains the mychomology region", *Proc. Natl. Acad. Sci. USA* 86:7092–7096.
Ebinuma, H. et al. (1997). "Selection of marker–free transgenic plants using the isopentenyl transferase gene", *Proc. Natl. Acad. Sci. USA* 94:2117–2121.
Barry, G.F. et al. (1984). "Identification of a cloned cytokinin biosynthetic gene", *Proc. Natl. Acad. Sci. USA* 81:4776–4780.

*Primary Examiner*—Lynette R. F. Smith
*Assistant Examiner*—Ousama Zaghmout
*Attorney, Agent, or Firm*—Rothwell, Figg, Ernst & Kurz, P.C.

[57] ABSTRACT

A chemically inducible promoter is described which may be used to transform plants with genes which are easily regulatable by adding plants or plant cells to a medium containing an inducer of the promoter or by removing the plants or plant cells from such medium. The promoter described is one which is inducible by a glucocorticoid which is not endogenous to plants. Such promoters may be used with a variety of genes such as ipt or knotted1 to induce shoot formation in the presence of a glucocorticoid. The promoter may also be used with antibiotic or herbicide resistance genes which are then regulatable by the presence or absence of inducer rather than being constitutive. Other examples of genes which may be placed under the control of the inducible promoter are also presented.

19 Claims, 8 Drawing Sheets

CHEMICAL INDUCIBLE PROMOTOR USED TO OBTAIN TRANSGENIC PLANTS WITH A SILENT MARKER

This application was made with Government support under DOE Grant #FG02-94ER20142, funded by the Department of Energy.

BACKGROUND OF THE INVENTION

Transgenic techniques have become a powerful tool to address important biological problems in multicellular organisms, and this is particularly true in the plant field. Many approaches that were impossible to implement by traditional genetics can now be realized by transgenic techniques, including the introduction of homologous or heterologous genes into plants, with modified functions and altered expression patterns. The success of such techniques often depends upon the use of markers to identify the transgenic plants and promoters to control the expression of the transgenes.

Selectable markers are widely used in plant transformation. Historically such markers have often been dominant genes encoding either antibiotic or herbicide resistance (Yoder and Goldsbrough, 1994). Although such markers are highly useful, they do have some drawbacks. The antibiotics and herbicides used to select for the transformed cells generally have negative effects on proliferation and differentiation and may retard differentiation of adventitious shoots during the transformation process (Ebinuma et al., 1997). Also, some plant species are insensitive to or tolerant of these selective agents, and therefore, it is difficult to separate the transformed and untransformed cells or tissues (Ebinuma et al., 1997). Further, these genes are constitutively expressed, and there are environmental and health concerns over inserting such constitutively expressed genes into plants which are grown outside of a laboratory setting (Bryant and Leather, 1992; Gressel, 1992; Flavell et al., 1992).

One marker which is neither an antibiotic nor a herbicide is the ipt gene. This gene encodes isopentenyltransferase which is used in cytokinin synthesis (Barry et al., 1984). Overproduction of cytokinins results in the overproduction of shoots (Barry et al., 1984). This overproduction of shoots can result in a phenotype having a large number of shoots (hereafter "shooty phenotype"). This phenotype can be used as a marker (Ebinuma et al., 1997). A chimeric ipt gene under the control of the cauliflower mosaic virus (CaMV) promoter has been introduced into cells of potato (Ooms et al., 1983), cucumber (Smigocki and Owens, 1989), and several Nicotiana species (Smigocki and Owens, 1988) and these transgenic cells proliferated and exhibited an extreme shooty phenotype and loss of apical dominance in hormone-free medium. Studies have shown that in plants transformed with ipt to overproduce cytokinins, the cytokinins work only locally as a paracrine hormone (Faiss et al., 1997). One problem with the use of ipt as a marker is that the resulting transgenic plants lose apical dominance and are unable to root due to overproduction of cytokinins (Ebinuma et al., 1997).

Ebinuma et al. (1997) developed one method to use the ipt marker and to overcome the problems noted above. They developed a vector in which the ipt gene was inserted into a plasmid which included the transposable element Ac. The construct included the T-DNA (portion of the Ti plasmid that is transferred to plant cells) and the 35S CaMV promoter. This construct was transformed into A. tumefaciens. Leaf segments were inoculated with the transformed bacteria and grown on nonselective media. Abnormal shoots with an extra shooty phenotype were selected and cultivated further for six months. From these, several normal shoots grew. Some of these were a result of the transposable element Ac having excised from the genome along with the ipt gene. This was determined by DNA analysis. Some of these few plants retained the other necessary markers which had also been included in the plasmid. This method therefore overcomes the problems of having a constitutively expressed ipt gene present. Unfortunately, this method requires many months of cultivation and results in only a few plants which have lost the ipt gene. Ebinuma et al. (1997) report that 6 months after infection the frequency of marker free plants was 0.032%.

The gene CKI1 was recently identified (Kakimoto, 1996). Overproduction of this gene in plants results in plants which exhibit typical cytokinin responses, including rapid cell division and shoot formation in tissue culture in the absence of exogenous cytokinin (Kakimoto, 1996). The CKI1 gene can be used as a selectable marker in a manner similar to ipt, i.e., the CKI1 gene can be put under the control of a promoter and overexpressed in transgenic plant cells thereby inducing shoot formation in the absence of exogenous plant hormones. Such shoots can be excised thereby obtaining transgenic plants. Such shoots, obtained either from cells transformed with ipt or CKI1, cannot be made to grow normally while the cells are expressing these transgenes. The knotted gene and knotted-like genes are a third group of genes which when overexpressed can lead to ectopic production of adventitious shoots (Chuck et al., 1996; Lincoln et al., 1994). These can be used as selectable markers in the same manner as the ipt and CKI1 genes.

Besides the use of markers to identify transgenic plants, the use of promoters to control the transgenes is a normal part of such experiments. In most experiments, the transgenes are transcribed from a strong promoter, such as the 35S promoter of the cauliflower mosaic virus (CaMV). However, a more flexible gene expression system is needed to extract greater benefits from transgenic technology. Good inducible transcription systems are desired because transgenic plants with inducible phenotypes are as useful as conditional mutants isolated by traditional genetics. In this regard, several induction systems have been reported and successfully used (Ainley and Key, 1990; Gatz et al., 1992; Mett et al., 1993; Weinmann et al., 1994). Among these, the tetracycline-dependent expression systems are the most advanced (for review, see Gatz, 1996).

The glucocorticoid receptor (GR) is a member of the family of vertebrate steroid hormone receptors. GR is not only a receptor molecule but also a transcription factor which, in the presence of a glucocorticoid, activates transcription from promoters containing glucocorticoid response elements (GREs) (for reviews, see Beato, 1989; Picard, 1993). It has been considered that the GR system could be a good induction system in plants because it is simple, and glucocorticoid itself does not cause any pleiotropic effects in plants. Nevertheless, a general and efficient glucocorticoid-inducible system using GR has not previously been constructed for transgenic plants, although it has been demonstrated that a system comprising GR and GREs could work in a transient expression system with cultured plant cells (Schena et al., 1991). On the other hand, it has been reported that the hormone-binding domain (HBD) of GR could regulate the function of plant transcription factors in transgenic plants (Aoyama et al., 1995; Lloyd et al., 1994).

The publications and other materials used herein to illuminate the background of the invention, and in particular cases to provide additional details respecting the practice, are incorporated herein by reference, and for convenience, are referenced by author and date in the text and respectively grouped in the appended List of References.

SUMMARY OF THE INVENTION

In one aspect, the invention relates to a vector which is useful for making transgenic plants. The vector is designed such that it includes a selectable marker which is chemically inducible rather than constitutive. The specific markers used in the Examples are the ipt and CKI1 genes which result in the selectable marker of a shooty phenotype although other marker genes can similarly be used. The marker gene is placed under the control of a glucocorticoid hormone transcriptional inducer. Any gene of interest can be included in the vector containing the marker gene and inducible promoter. After infection, transgenic cells can be selected by growing them in the presence of a hormone to induce transcription of the marker gene. After selection, the plants can be grown in the absence of the glucocorticoid and will grow normally. The transgene of interest is not under the control of the glucocorticoid and can be expressed in the transgenic plant under normal, hormone free conditions. The invention further involves methods of using the above described inducible vector.

By placing the ipt or CKI1 gene or one of the genes of the knotted family under the control of a glucocorticoid inducible promoter within a plasmid and using this to transform cells, growing such cells on MS medium without plant hormones but in the presence or absence of dexamethasone, a synthetic glucocorticoid analog, one can select for transformed cells. Since the cells are grown in the absence of plant hormones, shoots will develop only in cells that are transformed and overproducing cytokinins in the presence of dexamethasone. Nontransformed cells will not produce shoots and cells grown in the absence of dexamethasone will not produce shoots. Teratoma shoots should appear in 2–3 weeks on transformed cells grown in the presence of dexamethasone. These shoots can be excised and placed on MS medium containing indole acetic acid but without dexamethasone. Under this condition, the ipt, CKI1 or knotted gene should no longer be activated and after the cytokinin level has decreased to the normal level the transgenic plants should appear normal and fertile and be able to set seeds.

Another type of selectable marker which may be placed under the control of a glucocorticoid receptor inducible promoter are antibiotic or herbicide resistance genes. These can be made to express the resistance to an antibiotic or herbicide for purposes of selecting the transformed cells, but once the plant has been selected and is being grown in the absence of a glucocorticoid, the resistance gene will be repressed. This is more environmentally desirable than a system which leaves the transformed plants with a constitutively active antibiotic or herbicide resistance gene.

The chemically inducible system can be used more generally and of course is not limited to being used to induce the ipt, CKI1 or knotted gene or other selectable marker. It can be used to chemically induce any gene of interest. It can be used to induce a screenable marker, such as luciferase or other desired screenable marker.

The transcriptional induction system in the specific Examples does not use the entire glucocorticoid receptor protein but only its hormone-binding domain as a regulatory domain in a chimeric transcription factor. The transcription factor, designated GVG, also contains heterologous DNA-binding and transactivating domains from the yeast transcription factor GAL4 and the herpes viral protein VP16, respectively. The GVG gene was introduced into tobacco together with a luciferase (Luc) reporter gene transcribed from a promoter containing six copies of the GAL4 upstream activating sequence (GAL4 UAS). Good induction of both the luciferase activity and the Luc mRNA levels were observed upon glucocorticoid treatment. The advantages and potential uses of the glucocorticoid-inducible system are discussed.

BRIEF DESCRIPTION OF THE DRAWINGS

FIGS. 4A–C represent the induction of luciferase activity in Arabidopsis.

FIGS. 5A–B represent the kinetics of the Luc mRNA level induced by DEX. Transgenic tobacco plants carrying the GVG gene and the Luc reporter gene were first grown on agar medium for 14 days and then adapted to growth in a hydroponic medium for 3 days. DEX treatment was started by adding DEX to the medium at a final concentration of 10 $\mu$M (time indicated as 0). After 24 hours of treatment, DEX was then removed from the medium. Total RNA was prepared from 20 plants at each time indicated and subjected to Northern blot analysis. cDNA fragments of the firefly luciferase (FIG. 5A) and the GVG gene (FIG. 5B) were used as probes. Signals were imaged by the BAS-2000 system (Fuji Photo Films co.). Closed and open arrows indicate the time points of adding and removing DEX, respectively.

FIG. 6 shows the intensity and sustainability of induction by various glucocorticoids. Transgenic tobacco plants carrying the GVG gene and the Luc reporter gene were first grown on agar medium for 14 days and then transferred to a fresh agar medium containing 30 $\mu$M of different glucocorticoids for an additional 2 days. After the induction, plants were transferred back to the agar medium without glucocorticoid (time indicated as 0). Relative luciferase activities induced by DEX (●) triamcinolone acetonide (○), betamethasone (■) and hydrocortisone (□) are plotted. The value obtained with no glucocorticoid (the non-induction level) was arbitrarily set as 1.

DETAILED DESCRIPTION OF THE INVENTION

The present invention relates to transgenic plants which include a selectable marker which is under the control of an inducible promoter. Ideally, such a promoter will be one which can be turned on (induced) to select for cells or plants which have become transgenic but which will not be turned on under natural growth conditions. In this manner the selectable marker gene, although present in the transgenic plants, will be completely silent during the normal growth of the plants and should not interfere with the growth of the plants. Such a silent marker gene will also be more environmentally sound than, e.g., having an antibiotic resistance gene marker present wherein said resistance gene is expressed during the normal growth of the plant. The use of this latter type of marker is of concern because it may lead to the development of organisms resistant to the antibiotic.

One inducible promoter, which is the one used throughout the Examples which appear below, is the glucocorticoid receptor. This has been considered to be a good induction system for plants because glucocorticoid itself does not cause any pleiotropic effects in plants. The use of a steroid receptor domain to regulate gene expression in transgenic plants has been previously reported by Lloyd et al. (1994), who showed that trichome development in Arabidopsis could be successfully controlled by a chimeric protein comprising the glucocorticoid receptor domain and the maize transcriptional regulator R. However, the construction of such a chimeric transcription factor whose activity is tightly regulated by the glucocorticoid receptor domain is not always easy and achievable in every case. Tight regulation appears to be critically dependent on the intramolecular structure of the chimeric protein, especially the relative position between the glucocorticoid receptor domain and the domain whose function is to be regulated. The vector design described in the Examples below is one example of a construct in which there is tight regulation.

One selectable marker utilized in the instant studies is the ipt gene. When this gene is induced it results in a phenotype which is easily selected by visual inspection, this being the extreme shooty phenotype in which plant cells grow many shoots rather than roots. Once the inducing agent is removed, the ipt gene becomes silent and the cells are able to grow normally. Other selectable markers, e.g., the CKI1 gene may be used in a similar fashion. Again, whatever marker is used will be active only while induced and will be silent once the chemical inducer is removed.

The vectors to be used in forming transgenic plants will include a chemically inducible promoter which will activate the selectable marker. If desired, any other gene of interest can also be put under control of the inducible promoter such that the gene could be turned on whenever desired. Such a gene need not be a marker. Examples of such vectors are presented in the following Examples which describe not only the vectors, but the methods used to prepare and screen for transgenic plants containing such vectors.

A variety of DNA constructs can be made which incorporate the principle of using a chemical inducible marker. The theory behind the design of the plasmids, which are described in detail below, was to assemble regions within a plasmid which could be well controlled. Hormone-binding domains (HBDs) of vertebrate steroid hormone receptors are thought to have repressive effects on covalently linked, neighboring domains in the absence of their cognate ligands, and binding of the appropriate ligand to an HBD results in de-repression (Picard, 1993). This mechanism was taken advantage of by designing a transcription factor in which a constitutively active transactivating function was regulated by the HBD of the rat GR in cis (Picard et al., 1988; Rusconi and Yamamoto, 1987). A chimeric transcription factor comprising the DNA-binding domain of the yeast transcription factor GAL4 (Keegan et al., 1986) and the transactivating domain of the herpes viral protein VP16 (Triezenberg et al., 1988) was chosen as a constitutively active transactivating function. The chimeric protein produced, GAL4-VP16 was thought to act as a strong transcription factor in all cell types because the activation domain of VP16 is known to interact directly with general transcription factors, which are thought be evolutionarily conserved among eukaryotes (Goodrich et al., 1993; Lin et al., 1991; Sadowski et al., 1988). It has been shown that the HBD of the human estrogen receptor could regulate similar chimeric transcription factors in yeast and animal tissue culture cells (Braselmann et al., 1993; Louvion et al., 1993). Here, the HBD of the rat GR was added to the chimeric transcription factor and the resulting hybrid transcription factor was designated 'GVG' because it consisted of one domain each from GAL4, VP16 and GR. A DNA fragment encoding the GVG transcription factor was placed between the cauliflower mosaic virus 35S promoter (Odell et al., 1985) and the poly(A) addition sequence of the pea ribulose bisphosphate carboxylase small subunit rbcS-E9 (Coruzzi et al., 1984). As a binding site for GVG, a DNA fragment containing six copies of the GAL4 UAS (Giniger et al., 1985) was fused 5' to the minimal −46 to +9 region of the CaMV 35S promoter.

A major advantage of the GVG system in plants is the fact that GR and glucocorticoid, at least at the concentrations used, are nontoxic and have no observable adverse physiological effects on plants, thus allowing the induction of target genes without pleiotropic effects. To retain this advantage, all the other components in the GVG system were also obtained from non-plant sources.

A further advantage of the system is that glucocorticoid possesses characteristics that make it suitable as an inducer chemical. Because glucocorticoid can easily permeate plant cells, rapid gene induction can be performed using various methods. A local induction of gene expression can be obtained simply by spraying with a glucocorticoid solution. It is clear that inducer chemicals accumulate in leaves to a high concentration when whole plants are treated under open air conditions. Even under such conditions, the accumulated glucocorticoid does not cause any visible damage to leaves. As shown below, the induction level can be regulated by using different concentrations or different derivatives of glucocorticoid. This feature can be helpful for analyzing dose-dependent effects of induced gene products. Glucocorticoid is one of the best-studied biological compounds and over 100 different types of glucocorticoid derivatives are now available from commercial sources. Some of the glucocorticoid derivatives may be very stable in plants whereas others are rapidly degraded. These types of glucocorticoid would be useful for stable and transient induction, respectively. Moreover, some glucocorticoid antagonists might be used for down-regulation of induction.

Although specific constructs are described below, others may be easily envisioned and produced by one of skill in the art. The GVG system developed here is very flexible in its composition. For example, the transcriptional induction can be limited to a specific tissue by replacing the 35S promoter for the GVG gene with a tissue-specific promoter. Each functional domain in the GVG fusion protein is also exchangeable, allowing further refinement of the system. With a different DNA-binding domain and the HBD of another steroid hormone receptor, it is possible to develop another steroid induction system that can be used in combination with the GVG system.

The present invention is described by reference to the following Examples, which are offered by way of illustration and are not intended to limit the invention in any manner. Standard techniques well known in the art or the techniques specifically described below were utilized.

EXAMPLE 1

DNA Constructs

A) Construct pTA7002

Figure 1:
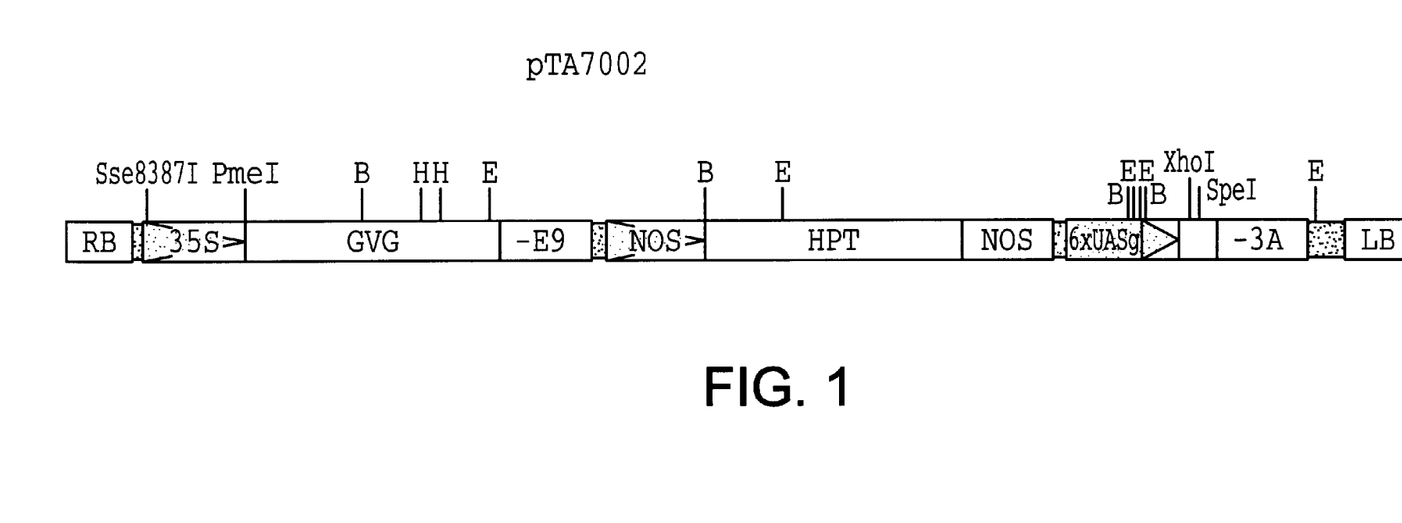
FIG. 1 is a schematic representation of the insert between the left and right borders in pTA7002. RB represents the right border and LB represents the left border. Restriction enzyme sites are shown above the drawing. The restriction enzyme sites represented by abbreviations are: B—BamHI, H—HindIII, E—EcoRI.

Plasmid pTA7002 is similar to pBI101 (Clontech) except that the sequence between the right border and the left border is replaced by three transcription units. The insert between the right and left borders of pTA7002 is illustrated in FIG. 1 and comprises a plasmid which includes the following elements: a 35S promoter, a GAL4 DNA binding domain, a VP16 transactivating domain, a glucocorticoid receptor hormone binding domain and a pea ribulose bisphosphate carboxylase small subunit rbcS-E9 poly(A) addition sequence all as part of a first transcription unit (35S-GVG-E9); a nopaline synthase (NOS) promoter, hygromycin phosphotransferase coding sequence, and the NOS terminator as part of a second transcription unit (NOS-HPT-NOS); and 6 tandem copies of a GAL4 upstream activating sequence (UAS) placed upstream of a minimal 35S promoter (−46 to +8) including the TATA region as part of a third transcription unit (6xUAS-(-46/35S)-3A). This third transcription unit also includes restriction sites (XhoI and SpeI) for insertion of any desired coding sequence and the pea ribulose bisphosphate carboxylase small subunit rbcS-3A (Fluhr et al., 1986). A coding region which is inserted in the XhoI-SpeI site should contain both the initiation and termination codons.

In more detail, the 35S-GVG-E9 transcription unit includes bases −343 to +9 of the CaMV 35S promoter (Odell et al., 1985). The GAL4 DNA binding domain comprises amino acids 1–74 (Laughon and Gesteland, 1984). The VP16 acidic domain comprises amino acids 413–490 (Dairymple et al., 1985). The GR receptor domain comprises amino acids 519–795 (Miesfeld et al., 1986). The 3' end of this transcription unit is the poly(A) addition sequence of the pea ribulose bisphosphate carboxylase small subunit rbcS-E9 (Coruzzi et al., 1984). The 35S promoter which drives the GVG gene can be changed to a promoter fragment of choice using the Sse8387i and PmeI restriction enzyme sites. By doing so, a promoter can be inserted which can induce the inserted gene in a specific tissue or during a specific period depending on the characteristics of the promoter.

B) pTA7001

This plasmid is identical with pTA7002 except for the orientation of the fragment containing 6xGAL4 UAS-TATA-cloning sites-3A terminator. Therefore it also contains both the cis- and trans-elements in the T-DNA region of the plasmid. The trans-element is the GVG region consisting of the GAL4 DNA binding domain, the VP16 transactivating domain, and the GR receptor domain driven by the 35S promoter. The cis-element consists of 6xGAL4 UAS and the TATA region of the 35S promoter. Again, this plasmid is based upon pBI101 (Clontech) with the region between RB and LB having been replaced. In pTA7001 this region has become:

1–39: pTiPOST37 from pBI101 (RB=1–25)
47–858: 35S promoter from pBI221 (TATA=813–816)
867–1097: GAL4 (aa 1–77)
1117–1340: VP16 (aa 413–490)
1347–2180: rat GR (aa 519–795)
2207–2764: pea rbcs-E9 terminator
2780–3112: NOS promoter from pBI101
3120–4145: hygromycin phosphotransferase
4147–4399: NOS terminator from pBI101
4893–4423: pea rbcs-3A terminator
4941–4894: cloning sites XhoI, SpeI
4995–4942: 35S promoter TATA region (TATA=4980–4977)
5197–4996: 6xGAL4 UAS
5198–5357: M13mmp19 EcoRI-HaeII fragment from pBI101
5358–5862: pTiPOST37 from pBI101 (LB=5838–5862).

C) pTA7002/ipt

This plasmid was prepared by inserting a restriction fragment (XhoI, SpeI) containing the isopentenyltransferase (ipt) gene of the pTiT37 plasmid (Goldberg et al., 1984) downstream of the 6xUAS promoter in the pTA7002 plasmid.

D) pMON721/Luc

Figure 2:
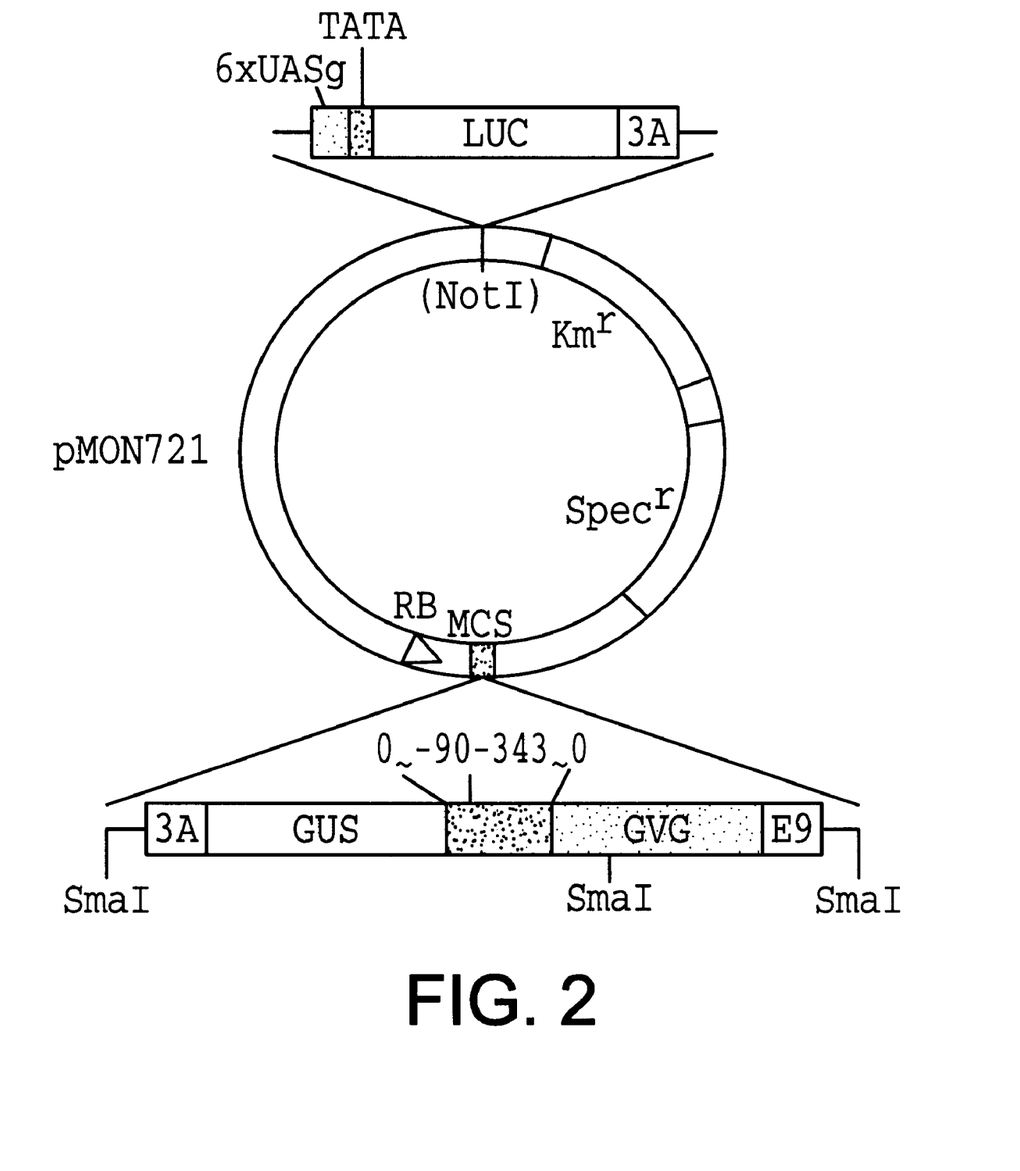
FIG. 2 illustrates the insertion points into pMON721 of the luciferase and the GVG constructs. The luciferase is inserted into the NotI restriction site. The GVG is inserted into the multicloning site of the vector.

This plasmid is similar in design to the pTA7002 plasmid in that it incorporates the same GVG system. However, this is based upon the pMON721 vector (Monsanto Corp., St. Louis, Mo.) rather than the pTA7002 plasmid. The GVG gene, which is transcribed from the −343 to +1 region of the CaMV 35S promoter (Odell et al., 1985), was flanked at the 3' end by the poly(A) addition sequence of the pea ribulose bisphosphate carboxylase small subunit rbcS-E9 (Coruzzi et al., 1984). The DNA fragments encoding specific domains were produced by the polymerase chain reaction (PCR) using primers of appropriate sequences for in-frame cloning. The GAL4 DNA binding domain comprises amino acids 1–74 (Laughon and Gesteland, 1984), the VP16 acidic domain comprises amino acids 413–490 (Dalrymple et al., 1985), and the GR receptor domain comprises amino acids 519–795 (Miesfeld et al., 1986). The GAL4 UAS DNA (5'-CGGGTGACAGCCCTCCG-3' SEQ ID NO:1) was synthesized chemically and the coding sequence for the Luc gene (de Wet et al., 1987) was excised from pGEM-luc (Promega Co.). The Luc coding sequence was transcribed from six copies of GAL4 UAS placed 5' to the −46 to +1 region of the 35S promoter and flanked at the 3' end by the poly(A) addition sequence of the pea rbcS-3A (Fluhr et al., 1986). FIG. 2 illustrates the points of insertion into pMON721 of the GVG and Luc nucleic acid constructs.

EXAMPLE 2

Plants Transformed with pMON721 Based Vectors

The vector pMON721 can be used in combination with A. tumefaciens strain ABI but is not used with A. tumefaciens strain LB4404. Strain ABI alone can induce shoots on tobacco leaf discs cultivated on MS medium without hormone and is therefore unusable for experiments in which the marker is the growth of shoots. The pMON721-A. tumefaciens strain ABI combination is useful for those experiments in which other markers are being screened, e.g., when one is selecting for antibiotic resistance. In these experiments the cells are grown in medium with hormones and selection is by kanamycin resistance, and they are grown both in the presence and in the absence of the inducer, e.g., dexamethasone.

A) Transformation of Plasmid into Bacteria

Plasmids were introduced into *Agrobacterium tumefaciens*. Plasmids derived from pMON721 were placed into strain ABI (Monsanto Corp., St. Louis, Mo.) by methods well known by those of skill in the art. For example, for pMON721/Luc, a single colony of *Agrobacterium tumefaciens* strain ABI (Monsanto Corp., St. Louis, Mo.) containing pMON721/Luc was selected from YEB plates containing 50 mg/L kanamycin, 25 mg/L chloramphenicol, 100 mg/L spectinomycin and 100 mg/L streptomycin. The Agrobacterium cells were transferred to a 50-mL sterile screw cap tube containing 10 mL YEB liquid medium with 50 mg/L kanamycin, 25 mg/L chloramphenicol, 100 mg/L spectinomycin and 100 mg/L streptomycin. The culture was grown at 28° C. for 24 hours. Agrobacterium cells in culture were collected by centrifugation at 3,000 rpm at 4° C. for 10 minutes. The cell pellet was washed once in 10 mL of YEB medium with antibiotics and then resuspended in 30 mL of B5 medium, which was used for inoculation of explants. YEB medium is prepared by bringing to 1.0 liter the following: 5.0 grams sucrose, 5.0 grams peptone, 5.0 grams beef extract, 1.0 gram yeast extract and 0.04 gram $MgSO_4 7H_2O$.

B) Co-cultivation with Agrobacteria

Leaf discs of *Nicotiana tabacum* cv SR1 were transformed and regenerated as described by Horsch et al. (1988) and transformation of Arabidopsis was performed according to the method of Valvekens et al. (1988).

C) Luciferase Containing Transgenic Plants

Primary transgenic plants were allowed to self-fertilize and seeds were collected. The transgenic progeny were germinated on MS medium (Murashige and Skoog, 1962) supplemented with 3% sucrose, 0.8% agar and 100 µg/mL kanamycin for selection. $T_3$ homozygous plants grown on the same agar medium for 14 days after germination were used in induction experiments. In some experiments, plants were transferred to a hydroponic growth medium containing 1/100 concentration of MS salts and adapted to the growth conditions for 3 days before use. In all cases, plants were exposed to continuous light and a temperature of 27° C. (tobacco) or 22° C. (Arabidopsis).

EXAMPLE 3

Plants Transformed with PTA7002 or PTA7001 Based Vectors

The vectors pTA7002 and pTA7001 may be used with *A. tumefaciens* strain LB4404. Unlike *A. tumefaciens* strain ABI, the LB4404 strain does not induce shoots and this combination of vector and bacterial strain may be used in those experiments in which the growth of shoots is the marker. The experiments described here used pTA7002/ipt. However, the vector used may include other genes of interest which are not under the control of the GVG system, which other genes it is desired to transform into plants. In these experiments, plants are selected on medium without hormones and without antibiotics, but in the presence and in the absence of inducer (e.g., dexamethasone). Only those cells grown in the presence of the inducer should generate shoots. These shoots are cut, placed in medium with auxins but without the inducer. The absence of the inducer stops the transcription of the ipt gene and auxin in the medium promotes root regeneration. These can then be tested by Northern blot analysis or for resistance to hygromycin to determine which regenerated plants in fact are transformed.

A) Transformation of Plasmid into Bacteria

Plasmids were introduced into *Agrobacterium tumefaciens*. Plasmids derived from pTA7002 or pTA7001 were placed into strain LB4404 (Clontech Laboratories, Inc.) by methods well known by those of skill in the art. For example, for pTA7002/ipt, a single colony of LB4404 containing pTA7002/ipt was selected from YEB plates containing 50 mg/L kanamycin and 100 mg/L streptomycin. The Agrobacterium cells were transferred to a 50-mL sterile screw cap tube containing 10 mL YEB liquid medium with 50 mg/L kanamycin and 100 mg/L streptomycin. The culture was grown at 28° C. for 24 hours. Agrobacterium cells in culture were collected by centrifugation at 3,000 rpm at 4° C. for 10 minutes. The cell pellet was washed once in 10 mL of YEB medium with antibiotics and then resuspended in 30 mL of B5 medium, which was used for inoculation of explants.

B) Co-cultivation with Agrobacteria

Tobacco leaves were cut into sections of 4 mm×4 mm on a wet sterile filter paper and then transferred to sterile, deionized water. The leaf sections were immersed for several minutes in the Agrobacteria solution (in B5 medium) in a petri dish. The sections were blotted dry on a piece of sterile filter paper and then placed on MBDK plates. MBDK media composition is: MS salts—4.3 g/L; B5 vitamins—112 mg/L; 2–4-D—0.5 mg/L; kinetin—0.1 mg/L; sucrose—20 g/L; phytogel—2 g/L; pH 5.7.

C) Shoot Regeneration

After 3 days of co-cultivation of tobacco leaves with Agrobacteria, the explants were washed 3 times by immersions in 30 mL sterile water containing 200 mg/L carbenicillin in a petri dish. After having blotted dry on sterile paper toweling, the explants were placed on MBC medium with or without dexamethasone (DEX, 30 µM). MBC media composition is: MS salts—4.3 g/L; B5 vitamins—112 mg/L; sucrose—20.0 g/L; carbenicillin—200 mg/L; phytogel—2.0 g/L; pH 5.7. The plates were incubated in a tissue culture room at 25° C. and 16 hour light/8 hour dark. After two weeks, green shoot buds appeared at wound sites of the explants only on medium containing DEX (30 µM). The shoots were excised and transferred to MBCI plates. MBCI medium is: MS salts—4.3 g/L, B5 vitamins—112 mg/L, sucrose—20.0 g/L, carbenicillin—200 mg/L, phytogel—2.0 g/L, pH 5.7, indole acetic acid (IAA)—0.15 mg/L.

D) Selection of Transgenic Plants

After 10 days of culture on MBCI plates, many adventitious shoots appear. These are cut and transferred to new MBCI plates. These shoots become normal looking after 10 days of culture. They regenerate roots and grow to plantlets of 4–6 leaves after 2–3 weeks. At this stage, they are ready to be tested to verify whether they are indeed transformed. Since the pTA7001 or pTA7002 plasmid contains a NOS-Hpt gene, transformed shoots should be resistant to hygromycin. Therefore, leaf samples containing petioles are excised and transferred to MBCI medium with 40 mg/L hygromycin for root induction. Only ~10% of the shoots collected are actually transformed. Nontransgenic cells may form shoots as a result of absorbing cytokinins produced from neighboring cells which are transformed and are producing cytokinins. Growth of the selected shoots in the presence of hygromycin can be used to select for transformed shoots. Northern or Southern blot analysis is another means of testing for transformation. These latter methods are useful in experiments in which the NOS-hpt gene has been deleted from the pTA7001 or pTA7002 plasmid and a gene of interest has been inserted in its place. Rooted shoots are transferred to pots and grown to maturity in a greenhouse. The transgenic plants appear normal and are fertile and set seeds.

EXAMPLE 4

Induction with Glucocorticoid

All glucocorticoid derivatives, dexamethasone (DEX), triamcinolone acetonide, betamethasone and hydrocortisone were purchased from Wako Pure Chemical Industries. The chemicals were dissolved in ethanol at 30 mM before use and diluted in either the growth medium or the spraying solution. The same volume of ethanol was added to negative control medium or solution. In the case of tissue culture experiments (as in Example 3) DEX is included in the tissue culture medium with phytogel. In the case of whole-plant treatment, plants were grown on an agar medium containing glucocorticoid or their roots were submerged in a hydroponic growth medium containing glucocorticoid at 0.01 mM. For the spraying method, the solution contained 30 $\mu$M DEX and 0.01% (w/v) Tween-20; the latter was added as a wetting agent. In experiments involving spraying of one half of a leaf, the other half and other parts of the plant were covered with a plastic film. It should be noted that although DEX is not an especially toxic chemical, it could have some physiological effect on a human and one should take precautions, especially the use of eye protection when one is spraying the compound.

EXAMPLE 5

Luciferase Assays

Extraction of luciferase and assays for relative luciferase activities were carried out as described by Millar et al. (1992). To image the luciferase luminescence, roots of plants treated with DEX were submerged in a solution containing 0.5 mM potassium luciferin (Sigma) for 1 hour or the petiole of a sprayed leaf was submerged in a solution of 0.5 mM potassium luciferin for 30 minutes. Potted plants were sprayed with a solution containing 0.5 mM potassium luciferin and 0.01% (w/v) Tween-20 and left for 30 minutes. The luciferase luminescence from plants was visualized using an image-intensifying camera (VIM) and photon-counting image processors (ARGUS-50) purchased from Hamamatsu Photonic Systems. The exposure time was 10 minutes. To take a picture of the luciferase luminescence from the sprayed leaf, the leaf and an instant color film (LP100, Fuji Photo films co.) were placed in contact with one another, with a thin plastic film between them, for 5 hours.

EXAMPLE 6

RNA Analysis

Total RNA isolation and Northern blot hybridization were performed as described by Nagy et al. (1988). After hybridization, signals were imaged with the BAS-2000 system (Fuji Photo Films Co.).

EXAMPLE 7

Selection of the Best Transgenic Lines

Several independent transgenic lines should be obtained and tested. One should select the best line as that which has a low basal level and a high induction level. Multicopies of T-DNA fragment are often inserted into one locus. In such a case, the 35S-promoter near the RB might happen to neighbor the inducible promoter and change the inducible promoter to a constitutively active promoter. Other than such a case, a chromosomal sequence neighboring the inducible promoter might also affect the activity. Therefore it is best to test the obtained transgenic lines to find one which has low basal activity and a high induction level.

EXAMPLE 8

Induction of Luciferase Activity in Transgenic Plants

Figure 3A:
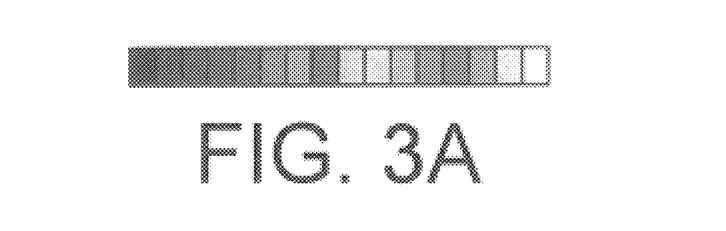
FIG. 3A is a scale showing the luminescence intensity from dark gray (lowest) to white (highest). Although shown as a scale of dark gray to white, in fact the luminescence is a blue color. This scale is used for interpreting the results of FIG. 3B.
Figure 3B:
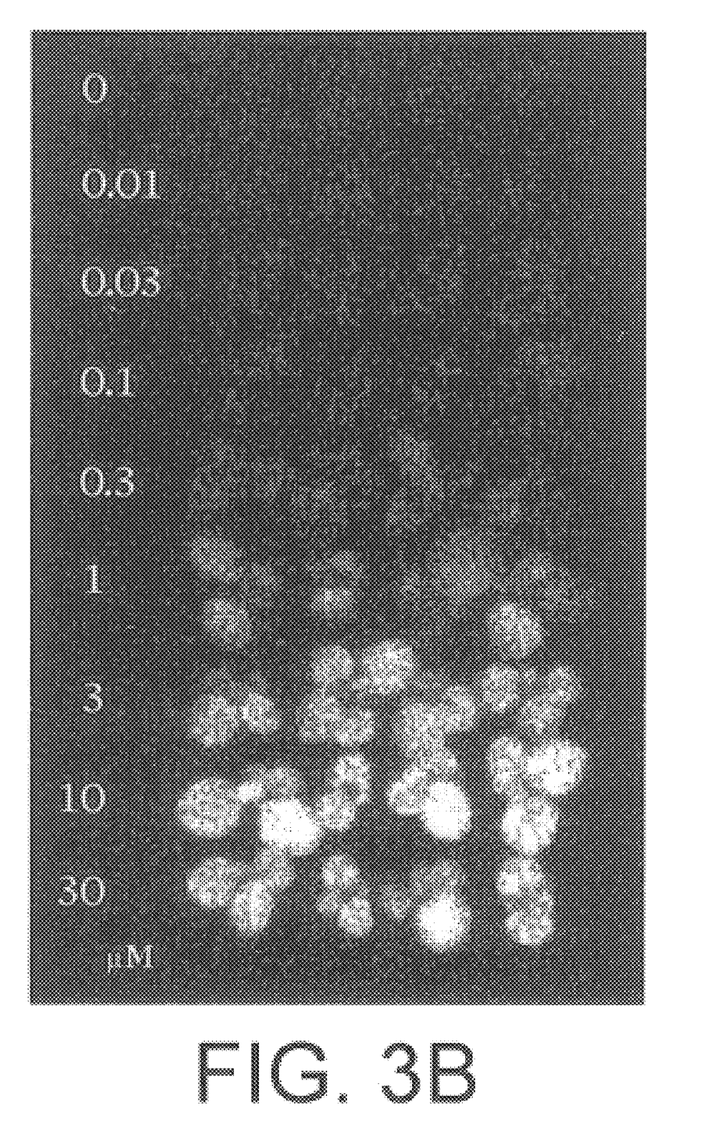
FIG. 3B shows the stationary expression levels of the luciferase activity induced by different concentrations of DEX.
Figure 3C:
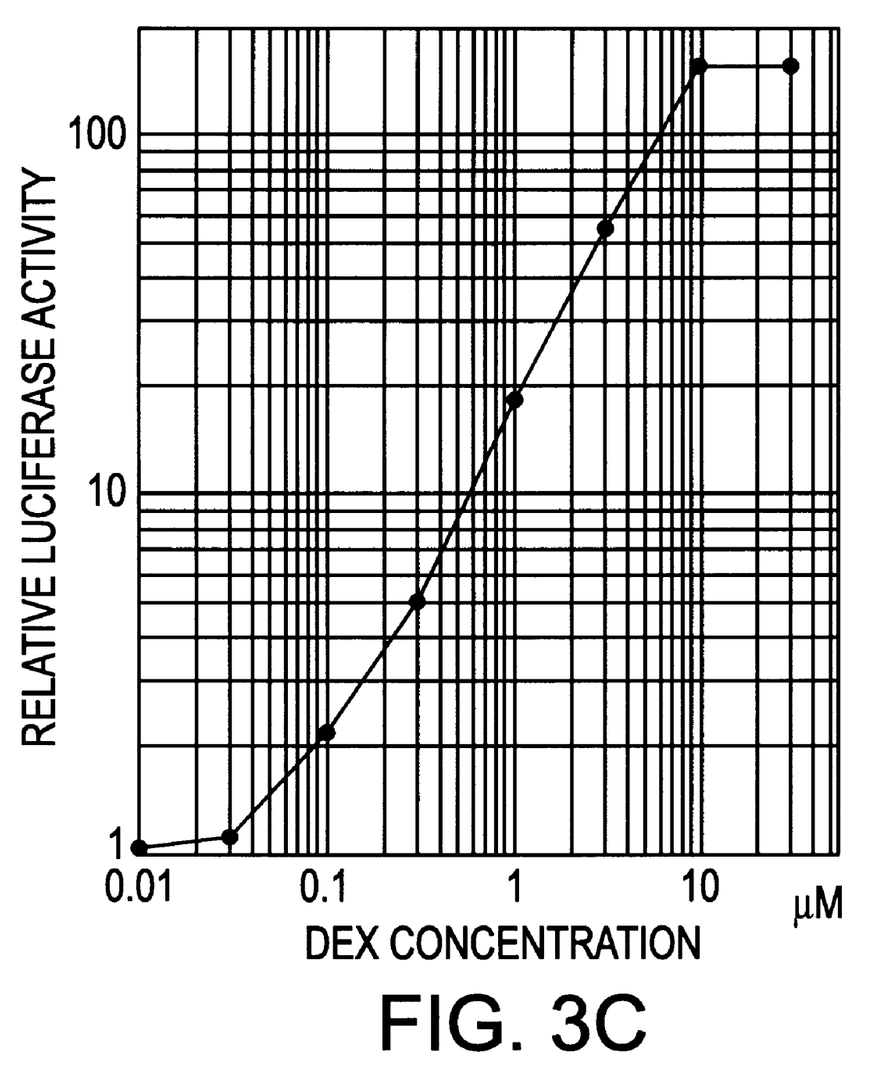
FIG. 3C shows the results of FIG. 3B plotted against DEX concentrations. The value obtained at 0 $\mu$M DEX (the basal, non-induction level) was arbitrarily set as 1.

Stationary induction levels of the luciferase activity were measured in response to different concentrations of a glucocorticoid. Young transgenic plants grown on an agar medium were transferred to a fresh agar medium containing different concentrations of DEX. After 2 days on the induction medium, whole cell lysate was prepared from 10 plants and assayed for luciferase activity. FIG. 3B shows an image of luciferase luminescence from plants using a high-sensitivity camera system. The color scale for FIG. 3B is shown in FIG. 3A. FIG. 3C shows the relative luciferase activity induced by different concentrations of DEX. The luciferase activity detected in the absence of DEX was very low and comparable to that obtained from transgenic plants carrying a luciferase gene preceded by the TATA region only (data not shown). This result indicates that the GAL4 UAS was quiescent in plants and not recognized by any endogenous plant transcription factor. Induction was detectable at a concentration of 0.1 $\mu$M DEX or higher, and a good correlation between DEX concentrations and induction levels was obtained in the concentration range from 0.1 to 10 $\mu$M. The maximum induction level was 100 times the basal level.

In this experiment, plants were treated with DEX for a sufficiently long period to ensure that the luciferase activity had reached a plateau for each DEX concentration. Induction was very slow in plastic wares, as observed in this experiment, probably because, under the enclosed conditions, transpirational water flow in plants and hence the uptake of glucocorticoid through the roots was slow compared with that under non-enclosed, open-air conditions. On the other hand, under the latter conditions, it is very difficult to precisely control the glucocorticoid concentration in plants because the hormone rapidly accumulates in leaves, as a result of transpiration.

Figure 4A:
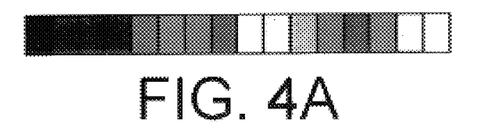
FIG. 4A is a color scale showing luminescence intensity from dark gray (lowest) to white (highest) (as in FIG. 3, the luminescence is blue, not gray as shown in the figure).
Figure 4B:
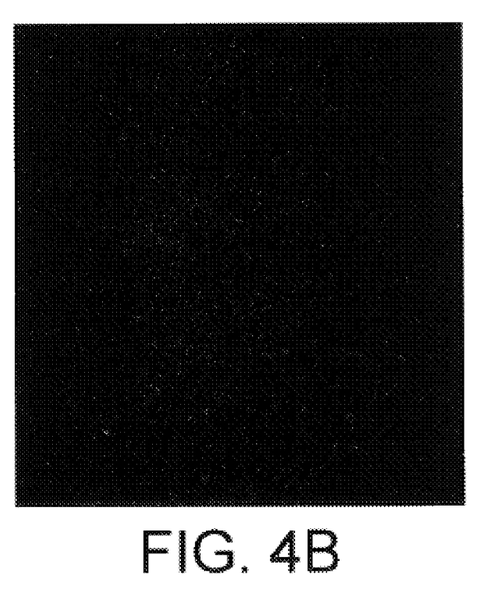
FIG. 4B represents a transgenic plant grown in a pot for 3 weeks and then sprayed with a solution containing 0.5 mM potassium luciferin and 0.01% (w/v) Tween-20 and assayed for luciferase activity.
Figure 4C:
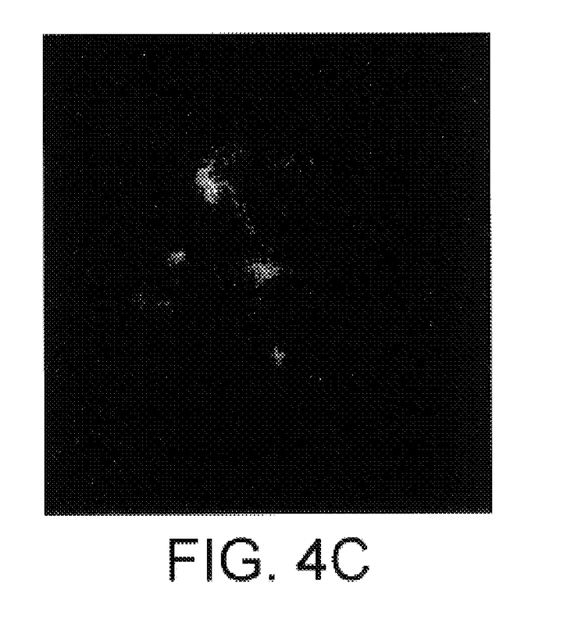
FIG. 4C represents the same plant as in FIG. 4B but here the plant was then sprayed with a solution containing 30 $\mu$M DEX and 0.01% (w/v) Tween-20. Twenty-four hours later, the plant was sprayed again with the luciferin solution and assayed. For both FIGS. 4B and 4C, the luminescence from the plant was imaged using a high-sensitivity camera system (Hamamatsu Photonic Systems). Heterogeneity of the luminescence seen in the plant treated with DEX was caused by uneven absorption of luciferin.

Various plant species have been employed for studies on basic and applied aspects of plant sciences, and among them, Arabidopsis has emerged as a model plant for basic explorations of plant biology. So far, however, good induction systems have not yet been developed for this model plant. Induction systems using plant promoters, e.g., heat-shock promoters, are not suitable because they elicit pleiotropic effects. Although the tetracycline-dependent expression system has been successfully used in tobacco, it does not appear to function in Arabidopsis (Gatz, 1996). On the other hand, it is seen here that the GVG system can also function in Arabidopsis. FIGS. 4A–C show that the luciferase activity in transgenic Arabidopsis was induced effectively by DEX. The GVG system should be widely applicable to many genes and in different species of transgenic plants.

EXAMPLE 9

Kinetics of the Transcriptional Induction by DEX

Figure 5A:
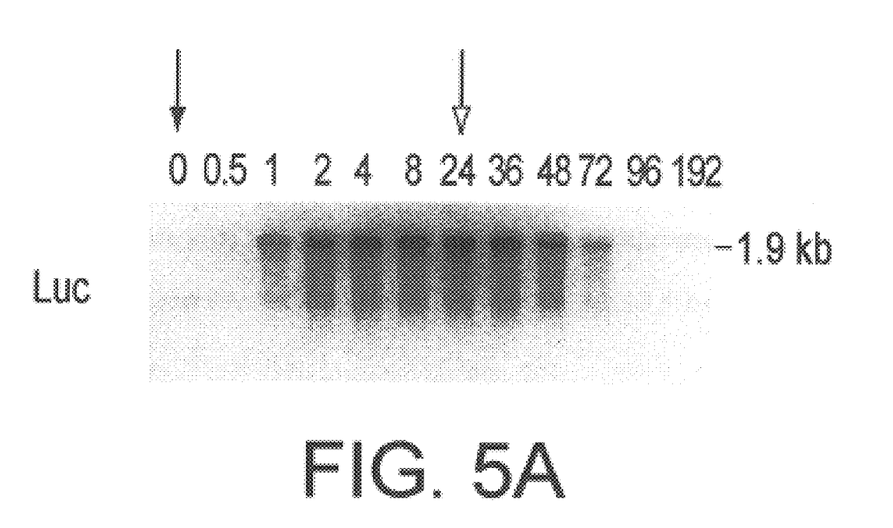
Figure 5B:
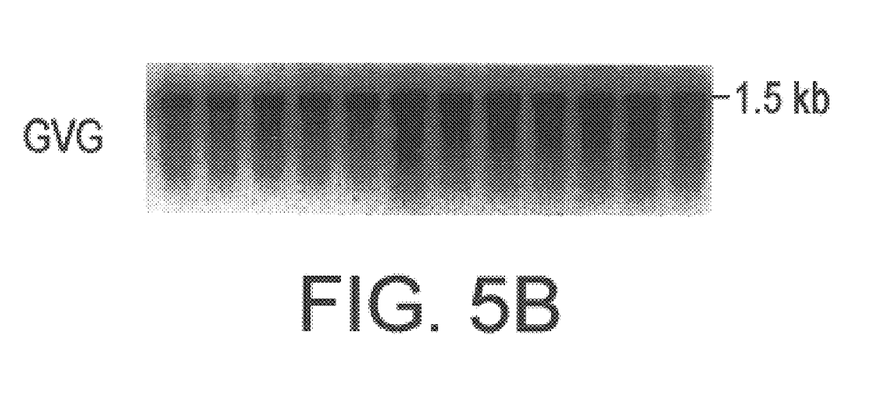

Although the luciferase activity is easy to measure, it is not suitable for kinetic study within a short time scale because the half-life of luciferase activity is estimated to be approximately 3 hours (Thompson et al., 1991). To obtain more direct information on the kinetics of induction, total RNA was prepared and subjected to Northern blot analysis. In these experiments, plants were placed in the open air to ensure rapid DEX uptake. Transgenic plants were adapted to hydroponic growth conditions in the open air and DEX was added to the liquid growth medium at a final concentration of 10 μM. Total RNA was prepared from 20 plants at each time point and subjected to Northern blot analysis. FIG. 4A shows that the Luc mRNA was first detected 1 hour after the addition of DEX and the amount increased to a stationary level within the next 3 hours. To examine the sustainability of the induction, DEX was removed from the medium and total RNA prepared from the plants was analyzed. FIG. 5A shows that Luc mRNA could be detected even 4 days after removal of DEX.

A similar result was obtained by monitoring the luciferase activity. Due to the high sensitivity of detection, the induced luciferase activity could be measured 30 minutes after DEX addition and for 8 days after removal of the hormone (data not shown). From these results, it can be concluded that the transcriptional induction by DEX is rapid and can be maintained for a long period.

EXAMPLE 10

Responses to Various Glucocorticoids

Figure 6:
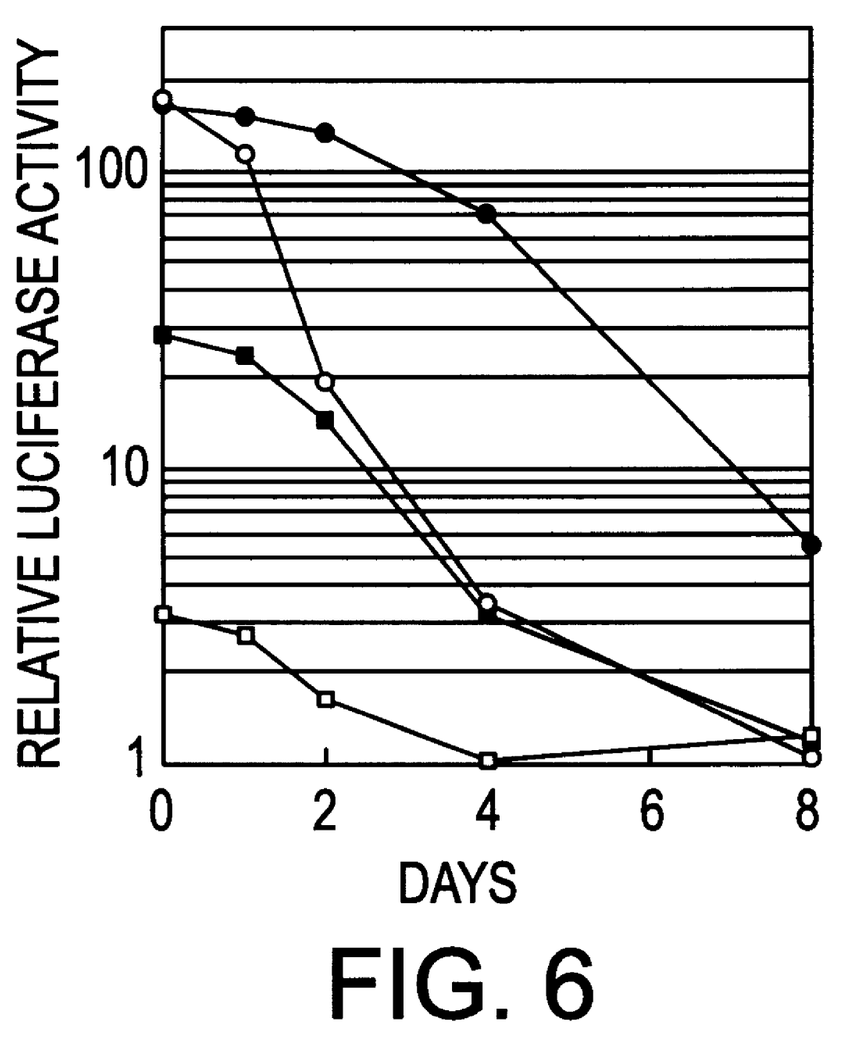

Different glucocorticoid derivatives were examined for the intensity and the duration of induction. Young transgenic plants grown on an agar medium were transferred to a fresh agar medium containing 30 μM of different glucocorticoids and grown for an additional 2 days. After the induction, plants were returned to the agar medium without glucocorticoid. At each time point indicated in FIG. 6, 10 plants were harvested and their luciferase activities assayed. FIG. 6 shows that the induction levels and their durations were different with different glucocorticoid derivatives. The highest induction levels were obtained with either DEX or triamcinolone acetonide. In contrast, only low or moderate induction levels were detected with betamethasone or hydrocorticoid, respectively. In these experiments, it was assumed that the induction level obtained with each glucocorticoid had reached a steady-state level because longer induction periods did not significantly increase the luciferase activity (data not shown). The induction by DEX was maintained for a longer period compared with that by triamcinolone acetonide, whereas both glucocorticoids conferred about the same induction level at the beginning of the treatment. Although the stability of these glucocorticoids in plants is not known in these experiments, the induction characteristics of different glucocorticoids might be used to regulate the intensity and the duration of induction.

EXAMPLE 11

Local Induction of Luciferase Expression by Glucocorticoid Spraying

Figure 7:
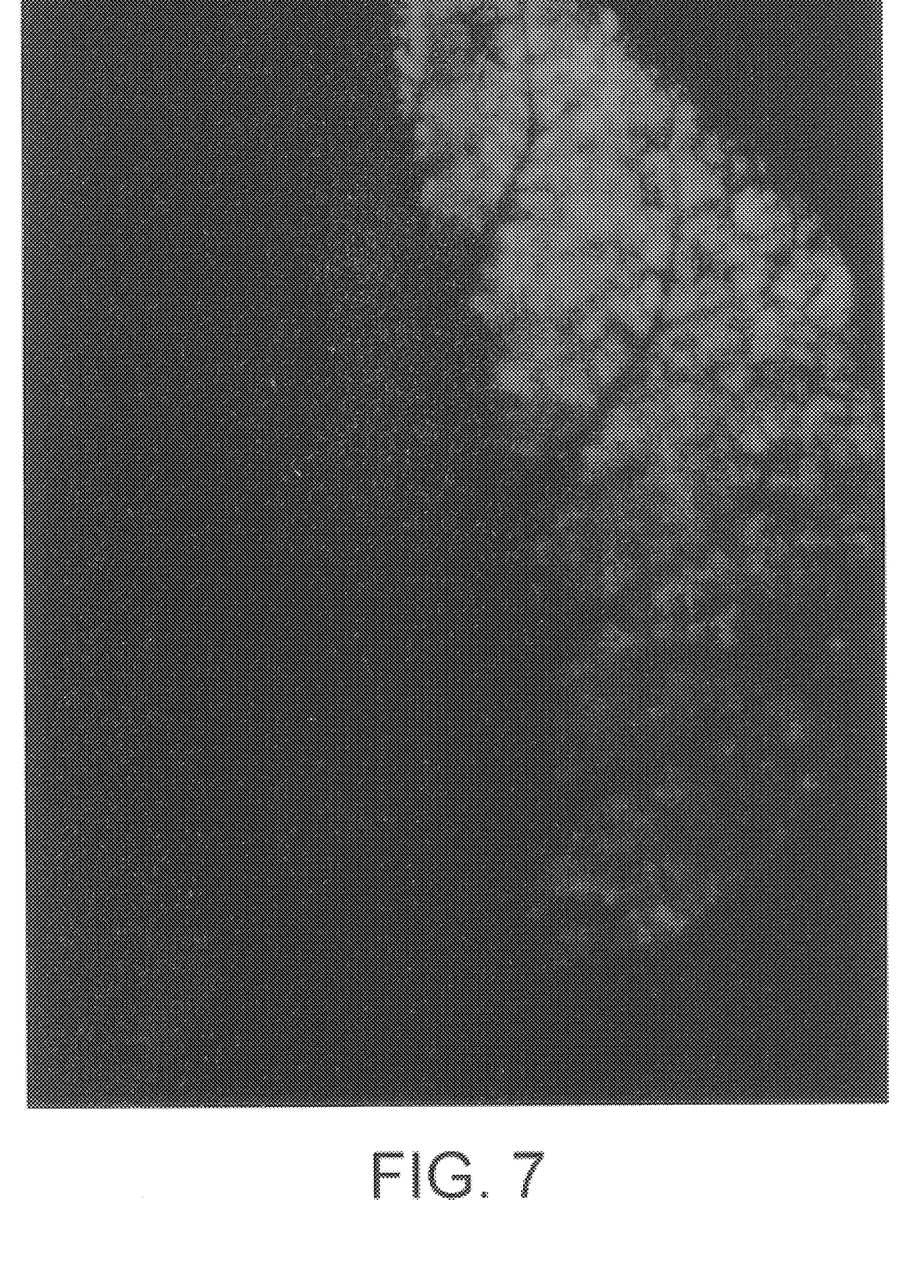
FIG. 7 shows the local induction of luciferase expression by glucocorticoid spraying.

The right and left halves of a leaf (about 10 cm in length) on a mature plant carrying the GVG and the Luc genes were sprayed with a solution containing 30 μM DEX and 0.01% (w/v) Tween-20 and a control solution, respectively. Twenty-four hours after spraying, the leaf was excised and allowed to take up luciferin through the petiole. FIG. 7 shows fluorescence from the portion of the leaf which had been treated with DEX whereas no fluorescence is seen in the portion of the leaf treated with a control solution without DEX. FIG. 7 was taken by placing an instant color film (Fuji Photo Films Co. LP100) on to the leaf, with thin plastic film in between them, for 5 hours.

EXAMPLE 12

Use of a Knotted Gene to induce Shoot Formation

The knotted1 gene and its family members, e.g., the knotted1 homologous genes KNAT1 and KNAT2, are highly expressed in shoots (Lincoln et al., 1994; Chuck et al., 1996). Transgenic plants which have been transformed with, e.g., the KNAT1 gene under the control of a CaMV 35S promoter have severe alterations including ectopic shoot formation (Lincoln et al., 1994). However, such shoots are unable to develop normally because of the uncontrolled expression of the knotted gene. A system in which plants are transformed with knotted genes which are regulatable will allow one to produce plants which will produce shoots and then to use the shoots to regenerate normal plants by shutting off the expression of the gene in the shoots. The present invention is one method of accomplishing such a result. A knotted gene, e.g., kn1 from maize, is placed in a vector such that it is under the control of the GVG system described above. Plants which have been transformed with this vector will grow normally in the absence of an inducer of the GVG system. Explants, e.g., leaf disks, of these transgenic plants can be treated with an inducer (e.g., dexamethasone) to stimulate the development of adventitious shoots. The developed shoots can be excised and transferred to a medium without the inducer. These shoots will then develop normally to yield transgenic plants. The vectors used may include other genes of interest, which are not under the control of the GVG system, which it is desired to transform into the plants. The selected plants will include the gene of interest and will have been selected without the requirement of using an antibiotic selectable marker. Note that the selection for transformed shoots should be performed as in Example 3, i.e., on medium without hormones (MBC) but with carbenicillin to kill Agrobacteria. Homologs of the maize knotted gene from other monocot or dicot plants may be used for the same purpose.

EXAMPLE 13

Use of a CKI 1 Gene to Induce Shoot Formation

The gene CKI 1 was recently identified (Kakimoto, 1996). Overproduction of this gene in plants results in plants which exhibit typical cytokinin responses, including rapid cell division and shoot formation in tissue culture in the absence of exogenous cytokinin (Kakimoto, 1996). The CKI1 gene can be used as a selectable marker in a manner similar to ipt. A system in which plants are transformed with CKI1 which is regulatable will allow one to produce plants which will produce shoots and then to use the shoots to regenerate normal plants by shutting off the expression of the gene in the shoots. The present invention is one method of accomplishing such a result. A CKI1 gene is placed in a vector such that it is under the control of the GVG system described above. Plants which have been transformed with this vector will grow normally in the absence of an inducer of the GVG system. Explants, e.g., leaf disks, of these transgenic plants can be treated with an inducer (e.g., dexamethasone) to stimulate the development of adventitious shoots. The developed shoots can be excised and transferred to a medium without the inducer. These shoots will then develop normally to yield transgenic plants. The vectors used may include other genes of interest, which are not under the control of the GVG system, which it is desired to transform into the plants. The selected plants will include the gene of interest and will have been selected without the requirement of using an antibiotic selectable marker. As in Examples 3 and 12, the selection is performed on MBC plates for shoots which are then transferred to MBCI for rooting.

EXAMPLE 14

Vectors with Antibiotic Resistance or Herbicide Resistance Genes under GVG Control Antibiotic resistance causing genes have been widely used in vectors as selectable markers. One problem with such systems is that these genes tend to be constitutively active and the transformed plants which are obtained will continue to express these genes. There have been environmental and health concerns over inserting such constitutively expressed genes into plants which are grown outside of a laboratory setting (Bryant and Leather, 1992; Gressel, 1992; Flavell et al., 1992). Placing such genes under the control of the GVG system overcomes these drawbacks. The antibiotic resistance genes will be expressed only during the selection process at the time when a glucocorticoid is present in the growth medium, but the genes will not be activated when grown outside of the laboratory in the absence of glucocorticoid. Any desired antibiotic resistance gene may be utilized. Appropriately modified pTA7001 and pTA7002 vectors can be utilized for this purpose. The antibiotic gene of interest is cloned into, e.g., the XhoI-SpeI cloning site. The pTA7001 or pTA7002 vectors will be modified such that the hpt gene is inactivated or removed. These modified vectors may be used. Suitable vectors can be prepared by starting with, e.g., the pBI101 (Clontech) vector. The region between the left and right borders of the vector is removed and replaced with the GVG system described above which includes, in brief, the 35S promoter, the GAL4 DNA binding domain, the VP16 transactivation domain, and the glucocorticoid receptor domain plus the 6xGAL4 UAS region followed by a cloning site. Such vectors do not include an endogenous antibiotic resistance gene. Any desired antibiotic gene can be inserted into the cloning site near the 6xGAL4 UAS region and will be under the control of the glucocorticoid. The hygromycin phosphotransferase gene and the neomycin phosphotransferase (npt) gene are two examples of antibiotic genes which may be utilized. Ti-vectors which include a DEX regulatable npt or hpt gene can be used to transform explants of the desired species. During the tissue culture phase, regenerated shoots will be selected in the presence of DEX (which activates the appropriate antibiotic resistance gene) and in the presence of the appropriate antibiotic (kanamycin or hygromycin). Once verified, transgenic shoots can then be transferred into tissue culture medium with the antibiotic but without the chemical inducer (DEX). The resulting plants will contain the antibiotic resistance genes but these genes will not be active in the absence of a chemical inducer.

Herbicide resistance genes can be similarly placed under GVG control and used for selection of transformed plants during tissue culture phase. Such plants would not express the herbicide resistance genes in the field. Examples of herbicide resistant genes are PAT (phosphinothricin acetyltransferase) which confers resistance to the BASTA herbicide (active ingredient phosphinothricin) (Rathore et al., 1993; Becker et al., 1992) and a mutant form of acetolactate synthase which is resistant to a sulfonylurea herbicide of DuPont (see, e.g., Wiersma et al., 1989; Harms et al., 1992; Hattori et al., 1992; Hattori et al., 1995). In theory these genes could be used not only as selectable markers in tissue culture but could also be expressed in the field. Because of the possible dangers of spraying DEX one would not want to spray DEX onto plants in a field, but this method could be used if a safer compound than DEX is used as an inducer.

While the invention has been disclosed herein by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

References

Ainley, W. M. and Key, J. L. (1990). *Plant Mol. Biol.* 14:949–966.

Aoyama, T., Dong, C.-H., Wu, Y., Carabelli, M. Sessa, G., Ruberti, I. Morelli, G. and Chua, N.-H. (1995). *Plant Cell* 7:1773–1785.

Barry, G. F., Rogers, S. G., Fraley, R. T. and Brand, L. (1984). *Proc. Natl. Acad Sci. USA* 81:4776–4780.

Beato, M. (1989). *Cell* 56:335–344.

Becker, D., Kemper, E., Schell, J. and Masterson, R. (1992). *Plant Molecular Biology* 20:1195–1197.

Braselmann, S., Graninger, P. and Busslinger, M. (1993). *Proc. Natl. Acad. Sci. USA* 90:1657–1661.

Bryant, J. and Leather, S. (1992). *Trends Biotechnol.* 10:274–275.

Chuck, G., Lincoln, C. and Hake, S. (1996). *The Plant Cell* 8:1277–1289.

Coruzzi, G., Broglie, R., Edwards, C. and Chua, N.-H. (1984). *EMBO J* 3:1671–1679.

Dalrymple, M. A., McGeoch, D. J., Davison, A. J. and Preston, C. M. (1985). *Nucl. Acids Res.* 13: 7865–7879.

de Wet, J. R., Wood, K. V., DeLuca, M., Helinski, D. R. and Subramani, S. (1987). *Mol. Cell. Biol.* 7:725–737.

Ebinuma, H., Sugita, K., Matsunaga, E. and Yamakado, M. (1997). *Proc. Natl. Acad. Sci. USA* 94:2117–2121.

Faiss, M., Zalubilová, Strnad, M. and Schmülling, T. (1997). *The Plant Journal* 12:401–415.

Flavell, R. B., Dart, E., Fuchs, R. L. and Fraley, R. B. (1992). *Bio/Technology* 10:141–144.

Fluhr, R., Moses, P., Morelli, G., Coruzzi, G. and Chua, N.-H. (1986). *EMBO J.* 5:2063–2071.

Gatz, C. (1996). *Curr. Opin. Biotechnol.* 7:168–172.

Gatz, C., Frohberg, C. and Wendenburg, R. (1992). *Plant J* 2:397–404.

Giniger, E., Varnum, S. and Ptashne, M. (1985). *Cell* 40:767–774.

Goldberg, S. B., Flick, J. S. and Rogers, S. G. (1984). *Nucl. Acids. Res.* 12:4665–4677.

Goodrich, J. A., Hoey, T. Thut, C. J., Admon, A. and Tjian, R. (1993). *Cell* 75:519–530.

Gressel, J. (1992). *Trends Biotechnol.* 10:382.

Harms, C. T., Armour, S. L., DiMaio, J. J., Middlesteadt, L. A., Murray, D., Negrotto, D. V., Thompson-Taylor, H., Weymann, K., Montoya, A. L., Shillito, R. D., et al. (1992). *Mol. Gen. Genet.* 233:427–435.

Hattori, J., Rutledge, R., Labbe, H., Brown, D., Sunohara, G. and Miki, B. (1992). *Mol. Gen. Genet.* 232:167–173.

Hattori, J., Brown, D., Mourad, G., Labbe, H., Ouellet, T., Sunohara, G., Rutledge, R., King, J. and Miki, B. (1995). *Mol. Gen. Genet.* 246:419–425.

Horsch, R., Fry, J., Hoffmann, N., Neidermeyer, J., Rogers, S. and Fraley, R. (1988). In *Plant Molecular Biology*

*Manual*, A5 (Gelvin, S. and Schilperoort, R., eds). Dordrecht, The Netherlands: Kluwer Academic Publishers, pp. 1–23.

Kakimoto, T. (1996). *Science* 274:982–985.

Keegan, L., Gill, G. and Ptashne, M. (1986). *Science* 231:699–704.

Laughon, A. and Gesteland, R. (1984). *Mol. Cell. Biol.* 4:260–267.

Lin, Y. -S., Maldonado, E., Reinberg, D. and Green, M. R. (1991). *Nature* 353:569–571.

Lincoln, C., Long, J., Yamaguchi, J., Serikawa, K. and Hake, S. (1994). *The Plant Cell* 6:1859–1876.

Lloyd, A. M., Schena, M., Walbot, V. and Davis, R. W. (1994). *Science* 266:436–439.

Louvion, J.-F., Havaux-Copf, B. and Picard, D. (1993). *Gene* 131:129–134.

Mett, V. L., Lockhead, L. P. and Reynolds, P. H. S. (1993). *Proc. Natl Acad. Sci. USA* 90:4567–4571.

Miesfeld, R., Rusconi, S., Godowski, P. J., Maler, B. A., Okret, S., Widstroem, A.-C., Gustafsson, J.-A. and Yamamoto, K. R. (1986). *Cell* 46:389–399.

Millar, A. J., Short, S. R., Chua, N.-H. and Key, S. A. (1992). *Plant Cell* 4:1075–1087.

Schena, M., Lloyd, A. M. and Davis, R. W. (1991). *Proc. Natl. Acad. Sci. USA* 88:10421–10425.

Smigocki, A. C. and Owens, L. D. (1988). *Proc. Natl. Acad. Sci. USA* 85:5131–5135.

Smigocki, A. C. and Owens, L. D. (1989). *Plant Physiol.* 91:808–811.

Thompson, J. F., Hayes, L. S. and Lloyd, D. B. (1991). *Gene* 103:171–177.

Triezenberg, S. J. Kingsbury, R. C. and McKnight, S. L. (1988). *Genes Devel.* 2:718–729.

Valvekens, D., Van Montagu, M. and Van Lijsebettens, M. (1988). *Proc. Natl. Acad. Sci. USA* 85:5536–5540.

Weinmann, P., Gossen, M., Hillen, W., Bujard, H. and Gatz, C. (1994). *Plant J* 5:559–569.

Wiersma, P. A., Schmiemann, M. G., Condie, J. A., Crosby, W. L. and Moloney, M. M. (1989). *Mol. Gen. Genet.* 219:413–420.

Yoder, J. I. and Goldsbrough, A. P. (1994). *Bio/Technology* 12:263–267.

---

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: double
      (D) TOPOLOGY: linear    (ii) MOLECULE TYPE: other nucleic acid
      (A) DESCRIPTION: /desc = "Synthetic DNA"

(iii) HYPOTHETICAL: NO

(xi) SEQUENCE DESCRIPTION: SEQ ID NO:1:

CGGGTGACAG CCCTCCG                    17

---

Murashige, T. and Skoog, F. (1962). *Physiol. Plant.* 15:493–497.

Nagy, F., Kay, S. A. and Chua, N.-H. (1988). In *Plant Molecular Biology Manual*, B4 (Gelvin, S. and Schilperoort, R., eds). Dordrecht, The Netherlands: Kluwer Academic Publishers, pp. 1–12.

Odell, J. T., Nagy, F. and Chua, N.-H. (1985). *Nature* 313:810–812.

Ooms, G., Kaup, A. and Roberts, J. (1983). *Theor. Appl. Genet.* 66:169–172.

Picard, D. (1993). *Trends Cell Biol.* 3:278–280.

Picard, D., Salser, S. J. and Yamamoto, K. R. (1988). *Cell* 54:1073–1080.

Rathore, K. S., Chowdhury, V. K. and Hodges, T. K. (1993). *Plant Molecular Biology* 21:871–884.

Rusconi, S. and Yamamoto, K. R. (1987). *EMBO J* 6:1309–1315.

Sadowski, I., Ma, J., Triezenberg, S. and Ptashne, M. (1988). *Nature* 335:563–564.

What is claimed is:

1. A method for selecting transgenic plants comprising a silent selectable marker wherein said method comprises the steps of:

a) transforming a plant cell with a vector wherein said vector comprises a gene selected from the group consisting of an ipt gene, a CKI1 gene or a gene from the knotted family, wherein said gene is under the control of an inducible promoter;

b) growing said plant cells in the absence of an exogenous plant hormone but in the presence of an exogenous inducer of said inducible promoter; and    c) excising shoots which develop,    wherein said shoots can grow into transgenic plants when grown in the absence of said inducer.

2. The method of claim 1 wherein said vector further comprises one or more genes of interest.

3. The method of claim 1 wherein said vector further comprises an antibiotic resistance gene.

4. The method of claim 1 wherein said vector further comprises a herbicide resistance gene.

5. The method of claim 1 which further comprises the step of:
(d) cultivating at least one of said shoots in the absence of said inducer to produce a transgenic plant.

6. The method of claim 3 wherein said shoots are further selected by growing said shoots in the presence of an antibiotic, said antibiotic being an antibiotic to which said antibiotic resistance gene confers resistance.

7. The method of claim 4 wherein said shoots are further selected by growing said shoots in the presence of a herbicide, said herbicide being a herbicide to which said herbicide resistance gene confers resistance.

8. The method of claim 1 wherein said vector comprises DNA encoding a hormone binding domain of a glucocorticoid receptor.

9. The method of claim 2 wherein said vector comprises DNA encoding a hormone binding domain of a glucocorticoid receptor.

10. The method of claim 3 wherein said vector comprises DNA encoding a hormone binding domain of a glucocorticoid receptor.

11. The method of claim 4 wherein said vector comprises DNA encoding a hormone binding domain of a glucocorticoid receptor.

12. The method of claim 6 wherein said vector comprises DNA encoding a hormone binding domain of a glucocorticoid receptor.

13. The method of claim 7 wherein said vector comprises DNA encoding a hormone binding domain of a glucocorticoid receptor.

14. The method of claim 8 wherein said inducer is selected from the group consisting of dexamethasone, triamcinolone acetonide, betamethasone and hydrocortisone.

15. The method of claim 9 wherein said inducer is selected from the group consisting of dexamethasone, triamcinolone acetonide, betamethasone and hydrocortisone.

16. The method of claim 10 wherein said inducer is selected from the group consisting of dexamethasone, triamcinolone acetonide, betamethasone and hydrocortisone.

17. The method of claim 11 wherein said inducer is selected from the group consisting of dexamethasone, triamcinolone acetonide, betamethasone and hydrocortisone.

18. The method of claim 12 wherein said inducer is selected from the group consisting of dexamethasone, triamcinolone acetonide, betamethasone and hydrocortisone.

19. The method of claim 13 wherein said inducer is selected from the group consisting of dexamethasone, triamcinolone acetonide, betamethasone and hydrocortisone.

* * * * *